(12) United States Patent  
Bennett

(10) Patent No.: US 9,114,054 B2  
(45) Date of Patent: *Aug. 25, 2015

(54) SYSTEM FOR MONITORING THE USE OF MEDICAL DEVICES

(75) Inventor: John A. Bennett, Villanova, PA (US)

(73) Assignee: Oakwell Distribution, Inc., King of Prussia, PA (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/547,502

(22) Filed: Jul. 12, 2012

(65) Prior Publication Data

US 2013/0023719 A1   Jan. 24, 2013

Related U.S. Application Data

(60) Provisional application No. 61/511,080, filed on Jul. 24, 2011.

(51) Int. Cl.

| | |
|---|---|
| *G08B 25/10* | (2006.01) |
| *H04Q 9/00* | (2006.01) |
| *A61M 27/00* | (2006.01) |
| *A61F 7/02* | (2006.01) |
| *A61H 9/00* | (2006.01) |
| *A61B 5/00* | (2006.01) |
| *G06F 19/00* | (2011.01) |
| *A61N 2/02* | (2006.01) |

(Continued)

(52) U.S. Cl.
CPC ............ *A61H 9/0078* (2013.01); *A61B 5/0002* (2013.01); *G06F 19/3418* (2013.01); *G06F 19/3481* (2013.01); *A61B 5/02042* (2013.01); *A61B 5/14551* (2013.01); *A61B 5/6826* (2013.01); *A61B 2505/07* (2013.01); *A61H 2201/5002* (2013.01); *A61H 2201/5012* (2013.01); *A61H 2201/5015* (2013.01); *A61H 2205/106* (2013.01); *A61H 2230/045* (2013.01); *A61H 2230/208* (2013.01); *A61N 2/02* (2013.01); *G08B 25/10* (2013.01)

(58) Field of Classification Search
CPC ........... G08B 25/10; H04Q 9/00; A61N 2/02; A61M 27/00
USPC .......... 340/539.1, 539.12; 600/123, 318, 301, 600/300; 601/152; 705/2
See application file for complete search history.

(56) References Cited

U.S. PATENT DOCUMENTS

| | | | | |
|---|---|---|---|---|
| 4,548,208 | A | * | 10/1985 | Niemi .............................. 600/14 |
| 4,641,633 | A | * | 2/1987 | Delgado .......................... 600/13 |

(Continued)

*Primary Examiner* — Fekadeselassie Girma

(74) *Attorney, Agent, or Firm* — Miller Law Group, PLLC

(57) ABSTRACT

A system for monitoring the use of a home-based medical apparatus providing medical therapy to a patient incorporates communication technology to permit communication from the operated component of the medical apparatus to a central station through one or more of Bluetooth® telephone communications, Smart Phone communications, Internet communications through a network, or other known or forthcoming communication devices. The operated medical apparatus can report any operational function to the central station for monitoring by medical professionals or caregivers, including the timing of any operation of the apparatus, the duration of operation, the effectiveness of the therapy, and malfunctions in the operation of the apparatus. The monitoring system is particularly adapted for use with inflation garment therapy and negative pressure wound therapy systems. The medical apparatus can also be provided with an RFD tag so that the medical apparatus, and perhaps the patient using the medical apparatus, can be found.

8 Claims, 4 Drawing Sheets

(51) Int. Cl.
*A61B 5/02* (2006.01)
*A61B 5/1455* (2006.01)

(56) References Cited

U.S. PATENT DOCUMENTS

| | | | |
|---|---|---|---|
| 4,683,873 A * | 8/1987 | Cadossi et al. | 600/14 |
| 5,348,008 A * | 9/1994 | Bornn et al. | 600/301 |
| 5,520,612 A * | 5/1996 | Winder et al. | 601/2 |
| 5,706,801 A * | 1/1998 | Remes et al. | 128/202.26 |
| 6,171,237 B1 * | 1/2001 | Avitall et al. | 600/300 |
| 6,231,528 B1 * | 5/2001 | Kaufman et al. | 601/2 |
| 6,736,786 B1 | 5/2004 | Shabty | |
| 6,768,425 B2 | 7/2004 | Flaherty et al. | |
| 6,852,089 B2 | 2/2005 | Kloecker et al. | |
| 7,009,511 B2 * | 3/2006 | Mazar et al. | 340/531 |
| 7,231,263 B2 | 6/2007 | Choi | |
| 7,566,295 B2 * | 7/2009 | Giardino et al. | 600/14 |
| 8,415,123 B2 * | 4/2013 | Pilla et al. | 435/173.1 |
| 8,460,223 B2 * | 6/2013 | Huster et al. | 601/44 |
| 8,571,655 B2 * | 10/2013 | Pastore et al. | 607/14 |
| 2003/0130567 A1 * | 7/2003 | Mault et al. | 600/300 |
| 2003/0216625 A1 * | 11/2003 | Phipps | 600/300 |
| 2003/0216787 A1 * | 11/2003 | Worden | 607/5 |
| 2004/0097842 A1 * | 5/2004 | Van Brunt et al. | 601/41 |
| 2004/0117204 A1 * | 6/2004 | Mazar et al. | 705/2 |
| 2004/0122297 A1 * | 6/2004 | Stahmann et al. | 600/300 |
| 2004/0130446 A1 * | 7/2004 | Chen et al. | 340/539.12 |
| 2005/0040954 A1 * | 2/2005 | McNally | 340/573.3 |
| 2006/0152373 A1 * | 7/2006 | King | 340/573.1 |
| 2007/0049853 A1 | 3/2007 | Adams et al. | |
| 2007/0173681 A1 * | 7/2007 | Giardino et al. | 600/9 |
| 2007/0249976 A1 | 10/2007 | Tucker et al. | |
| 2007/0299539 A1 * | 12/2007 | Othman et al. | 623/23.72 |
| 2008/0000477 A1 * | 1/2008 | Huster et al. | 128/204.23 |
| 2008/0027509 A1 * | 1/2008 | Andino et al. | 607/50 |
| 2008/0312547 A1 * | 12/2008 | Wada | 600/534 |
| 2009/0105554 A1 * | 4/2009 | Stahmann et al. | 600/300 |
| 2009/0131838 A1 * | 5/2009 | Fotiadis et al. | 601/2 |
| 2009/0163762 A1 * | 6/2009 | Setti et al. | 600/14 |
| 2009/0192421 A1 * | 7/2009 | Huster et al. | 601/44 |
| 2010/0174343 A1 * | 7/2010 | Andino et al. | 607/50 |
| 2011/0030141 A1 * | 2/2011 | Soderberg et al. | 5/600 |
| 2011/0270331 A1 * | 11/2011 | Peters et al. | 607/3 |
| 2012/0041403 A1 * | 2/2012 | Bennett et al. | 604/319 |
| 2012/0130327 A1 * | 5/2012 | Marquez Canada | 604/319 |
| 2012/0158074 A1 * | 6/2012 | Hall | 607/5 |
| 2012/0191018 A1 * | 7/2012 | Willeford | 601/2 |
| 2012/0191026 A1 * | 7/2012 | Aali et al. | 602/43 |
| 2012/0191159 A1 * | 7/2012 | Willeford | 607/51 |
| 2013/0023719 A1 * | 1/2013 | Bennett | 600/13 |
| 2013/0178695 A1 * | 7/2013 | Heiter-Kelly | 600/28 |
| 2013/0204106 A1 * | 8/2013 | Bennett | 600/324 |
| 2014/0018637 A1 * | 1/2014 | Bennett et al. | 600/301 |
| 2014/0058344 A1 * | 2/2014 | Toth | 604/319 |

* cited by examiner

SYSTEM FOR MONITORING THE USE OF MEDICAL DEVICES

CROSS-REFERENCE TO RELATED APPLICATIONS

This application claims domestic priority from U.S. Provisional Application Ser. No. 61/511,080, filed on Jul. 24, 2011, the content of which is incorporated herein by reference.

FIELD OF THE INVENTION

The present invention relates generally to system for monitoring the utilization and results from therapy, particularly therapy conducted at home by a patient, more specifically, to a system for monitoring the use of inflatable garment therapy to enhance the flow of blood from a patient's extremities through the use of an off-site server providing information to the patient's health provider.

BACKGROUND OF THE INVENTION

Inflatable garment therapy consists of a shaped inflatable garment, such as a garment adapted for wearing on the foot or the lower part of a patient's leg, that is coupled to a pump that cycles air under pressure into the garment to fill sequentially cells within the inflatable garment to push venous blood from the patient's extremity toward the patient's heart. In a different clinical condition, the inflatable garment can rapidly expand to mimic muscle contraction and promote peripheral circulation at extremities. In one form of inflatable garment therapy, the inflatable garment is constructed with multiple inflatable cells that can be inflated from the cell most distant from the heart in a sequential pattern to the cell closest to the heart. Then, the pressure is released and the cells are subsequently inflated through another cycle. This inflatable garment therapy is utilized primarily by patients at home, usually with the assistance of a visiting nurse that visits the patient periodically, but at the direction and supervision of a doctor.

The health care provider rarely knows how effective the inflatable garment therapy is for the patient. Although the visiting nurse will stop at the patient's home to check on the patient periodically, perhaps once every two weeks, and the health care provider will likely see the patient less frequently than the visiting nurse, this therapy should be conducted multiple times each day. Accordingly, the health care provider typically has little or no feedback as to whether the therapy is actually being done, or if the therapy is producing positive results. Further, the patient has no feedback as to the effectiveness of the therapy. Particularly since positive feedback will normally stimulate and encourage the continued use of the therapy, providing the patient with ongoing results of the therapy has a synergistic effect on the effectiveness of the therapy.

Inflatable garment therapy is not the only kind of in-home therapy that would have benefits associated with on-going monitoring. For example, negative pressure bandages are applied to wounds to extract exudates from the wound through the operation of a pump providing a negative pressure on the bandage sealed over the patient's wound site. The volume of the exudates, as well as the quality of the exudates, can provide a health care provider important information as to the effectiveness of the operation of the negative pressure bandage and as to the status of the patient's wound. Monitoring of any in-home therapy that is not being conducted at the immediate and constant supervision of a health care professional can be enhanced through monitoring. Even monitoring the use of medication by a patient can enhance the effectiveness of the medication for the patient. In bone growth stimulation therapy, such as electromagnetic or electrical devices that are applied to spinal fusion surgical sites to stimulate bone fusion, monitoring the use of the therapy device can provide the patient and the medical professionals responsible for the patient's care with important information as to how and when the electromagnetic fields are being applied.

In U.S. Pat. No. 7,231,263, granted to Soo Bong Choi on Jun. 12, 2007, a control system for utilizing an insulin pump is disclosed. The Choi system operates to provide security and control over the operation of an insulin pump. Before the pump can be utilized, the person logging in to the system provides an appropriate identification. The blood sugar level for the patient is ascertained and the amount of insulin to be injected is adjusted when the person logged in is the patient's health care provider. A Bluetooth module is utilized to make the communication between the insulin pump module and the internet.

A remote control for a medical apparatus is disclosed in U.S. Pat. No. 6,768,425, issued on Jul. 27, 2004, to J. Christopher Flaherty, et al, wherein the medical treatment apparatus has a local processor having a communications unit associated with it. The hand remote control includes a remote processor and an associated remote communication component that can communicate with the local processor in a wireless manner. Accordingly, the medical device can be operated with the operation of the remote control device without requiring the patient to manually access the medial apparatus.

In U.S. Patent Application Publication No. 2007/0249976, published on Oct. 25, 2007, a control apparatus for an inflatable garment therapy device is disclosed wherein the pump apparatus is self-contained within therapy device. U.S. Patent Application Publication No. 2007/0049853, published on Mar. 1, 2007, discloses the inflatable garment therapy device used to improve blood circulation in patient's extremities. Similarly, U.S. Pat. No. 6,852,089, issued on Feb. 8, 2005, to Richard J. Kloecker, et al, discloses an inflatable garment therapy device for a patient's arms. In U.S. Pat. No. 6,736,786, granted to Paul Shabty on May 18, 2004, a counterpulsation device is disclosed in which the operation of the inflatable cuff is coupled to a microprocessor to take the EKG of the patient so that the cuff inflation can be timed with the patient's EKG.

It would be desirable to provide a system for monitoring the operation and the effectiveness of therapy conducted by the patient in his home. It would also be desirable to provide feedback to the patient and to the health care provider as to the effectiveness and as to the utilization of the therapy.

SUMMARY OF THE INVENTION

It is an object of this invention to overcome the disadvantages of the prior art by providing a system for monitoring the use of medical devices.

It is another object of this invention to provide a monitoring system that can track and record the utilization of therapy incorporating medical devices, such as an inflation garment therapy or negative pressure wound therapy.

It is a feature of this invention that the utilization information can be transmitted to a remote server for access by medical professionals.

It is another feature of this invention that the medical device can be programmed to provide a notification to predetermined medical professionals when certain utilization parameters are encountered.

It is an advantage of this invention that a sensor on the medical apparatus to detect the unexpected presence of blood or other fluids It is another advantage of this invention that the medical apparatus can report to a central station monitored by caregivers as to the timing and duration of use of the medical device by the patient.

It is still another feature of this invention that the medical apparatus can report a malfunction of the medical apparatus to a central station.

It is still another advantage of this invention that the caregiver monitoring the central station can be alerted to any malfunction in the operation of the medical apparatus so that repair or replacement of the medical apparatus can be arranged promptly.

It is yet another feature of this invention that the effectiveness of the therapy utilizing the medical device can be monitored by professional caregivers.

It is yet another advantage of this invention that changes in the operative parameters of the medical device can be determined from a remote location through monitoring of the central station to which information about the operation of the medical apparatus is transmitted.

It is still another object of this invention to provide a monitoring of the use and operation of a medical apparatus used in patient therapy in a home environment.

It is yet another object of this invention to place an RFD tag on the medical apparatus so that the medical apparatus can be located and identified.

It is a further feature of this invention that the medical apparatus can be provided with a selected communication technology to report the use and operation of the medical apparatus to a central station or directly to a professional caregiver.

It is a further advantage of this invention that the communication technology can be used to communicate by Bluetooth® technology through a telephone system, to a Smart Phone or via the Internet.

It is another advantage of this invention that medical professionals and caregivers can more effectively treat the patients during home visits because of the advance knowledge from a central station related to the use, operation and effectiveness of the medical therapy utilizing a monitored medical apparatus.

It is yet another object of this invention to monitor the operation of a home-based negative pressure wound therapy apparatus to detect the operation of the pump, the length of time the pump is operated, the amount of exudates gathered by the apparatus, the quality of the collected exudates, the presence of blood in the collected exudates, and any malfunctions in the operation of the apparatus, including a broken seal on the bandage.

These and other objects, features and advantages are accomplished according to the instant invention by providing a system for monitoring the use of a home-based medical apparatus providing medical therapy to a patient. The monitoring system incorporates communication technology to permit communication from the operated component of the medical apparatus to a central station through one or more of Bluetooth® telephone communications, Smart Phone communications, Internet communications through a network, or other known or forthcoming communication devices. The operated medical apparatus can report any operational function to the central station for monitoring by medical professionals or caregivers, including the timing of any operation of the apparatus, the duration of operation, the effectiveness of the therapy, and malfunctions in the operation of the apparatus. The monitoring system is particularly adapted for use with inflation garment therapy and negative pressure wound therapy systems. The medical apparatus can also be provided with an RFD tag so that the medical apparatus, and perhaps the patient using the medical apparatus, can be found.

BRIEF DESCRIPTION OF THE DRAWINGS

The foregoing and other objects, features, and advantages of the invention will appear more fully hereinafter from a consideration of the detailed description that follows, in conjunction with the accompanying sheets of drawings. It is to be expressly understood, however, that the drawings are for illustrative purposes and are not to be construed as defining the limits of the invention.

DETAILED DESCRIPTION OF THE PREFERRED EMBODIMENT

Figure 1:
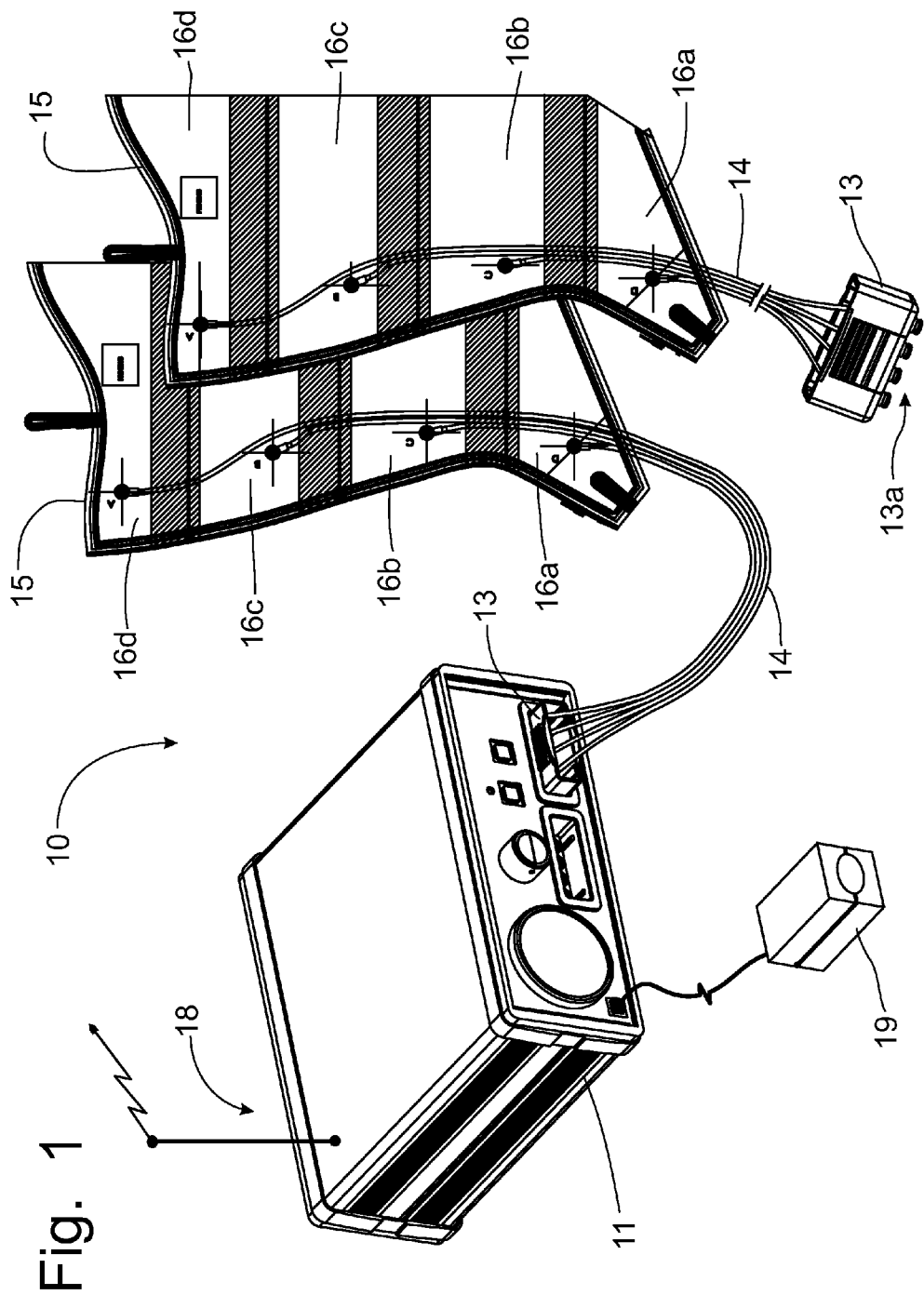
FIG. 1 is a schematic perspective view of an inflation garment therapy apparatus incorporating the principles of the instant invention.

Referring to the FIG. 1, a representative in-home therapy device in the form of an inflatable garment therapy apparatus 10, incorporating the principles of the instant invention, can best be seen. This particular therapy apparatus 10 includes an electrically powered pump 11 coupled to inflatable garments 15 by respective conduit assemblies 12 having a clip 13 formed with multiple ports 13a connected to individual conduit lines 14. Each of the conduit lines 14 are coupled to a corresponding one of the inflation cells 16a-16d.

The pump 11 is programmed to divert air under pressure to the inflation cell 16a most distant from the patient's heart, which because the depicted garments 15 are intended for utilization on a patient's lower legs is the lowermost inflation cell 16a. The pump 11 then inflates the next higher inflation cell 16b until the entire garment 15 is inflated, whereupon all of the inflation cells 16a-16d are deflated and the cycle of inflation of the cells 16a-16d restarts. The sequential pressurization of the inflation cells 16a-16d aids the circulation of blood from the veins in the extremity back to the patient's heart.

An improvement to the inflation garment apparatus 10, as seen in FIG. 1, is the operative connection of a pulse oximeter 19, which is a device that is placed in contact with the body of the patient, such as onto the patient's fingernail, to measure the percentage of oxygen saturation in the patient's blood and to sense the patient's heart beat. By coupling the monitoring of the patient's heart beat with the pulse oximeter 19 to the operation of the pump 11, the sequential inflation of the garment cells 16a-16d can be timed with the increase in blood pressure from the pulse of blood sent from the heart through the patient's arteries. For inflatable garments 15 for use on the lower extremities, the placement of the pulse oximeter 19 on a toenail of the patient could produce the most pertinent timing for the use of the apparatus 10. In addition, the pulse oximeter 19 provides a feedback to the patient in the form of the oxygen saturation percentage. The use of the inflation garment apparatus 10 to assist in the flow of blood back to the heart and lungs, where the blood becomes oxygenated, should result in an increased oxygen saturation percentage that will be sensed by the pulse oximeter 19. Thus, as the inflatable garment therapy is conducted, the patient should be able to see a positive feedback in the form of an increased oxygen saturation percentage that the therapy is working.

Figure 2:
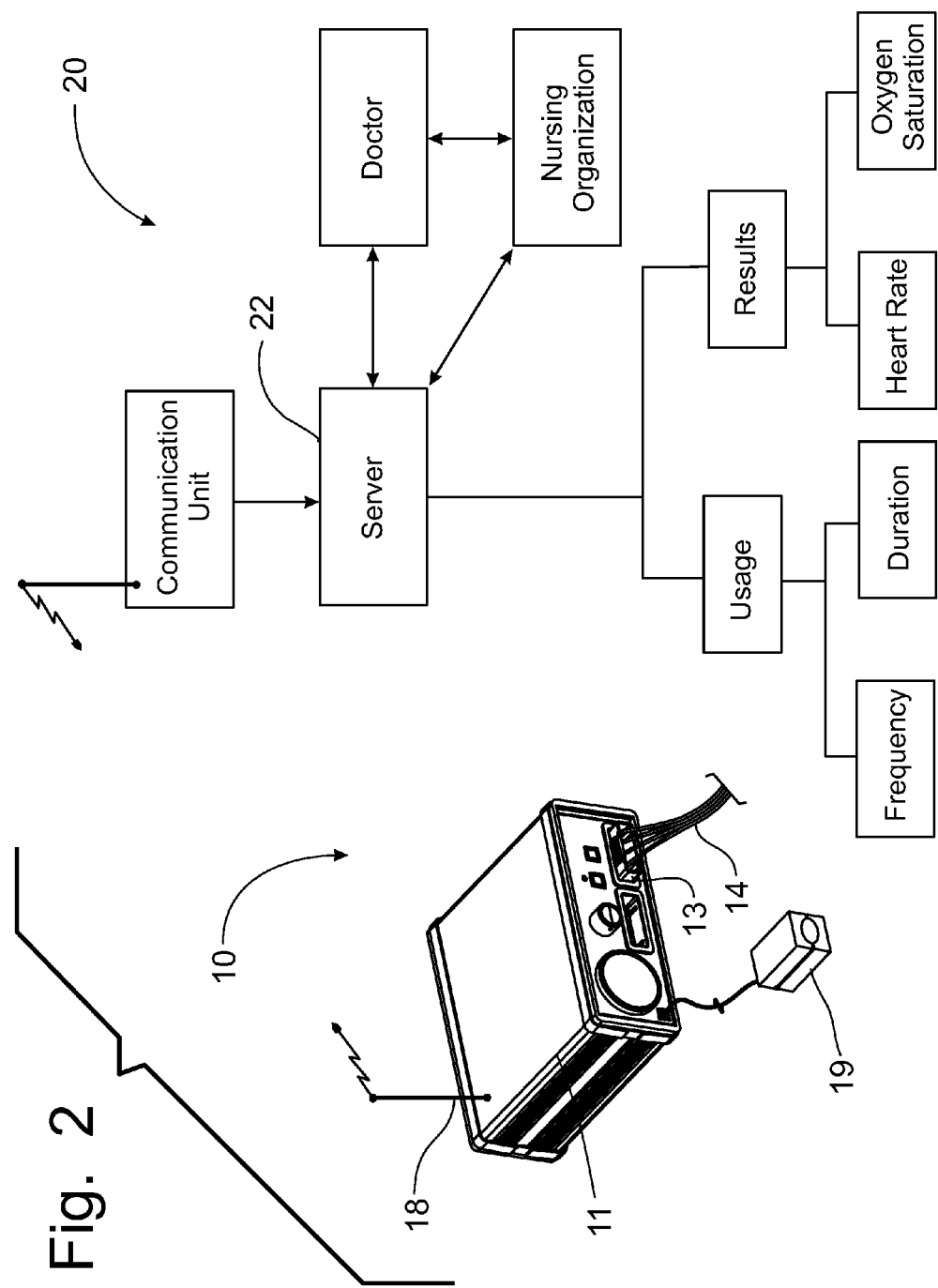
FIG. 2 is a schematic diagram of the system incorporating the principles of the instant invention.

Referring now to FIG. 2, the monitoring system 20 receives a signal from the inflation garment apparatus 10 to indicate utilization of the therapy device and the heart rate and the oxygen saturation percentage of the patient from the communication unit 18 of the apparatus 10, such as a Bluetooth® connection. The monitoring system 20 receives the signal from the communications unit 18 and transfers the information received to a server 22 that is remote from the home location of the patient. Included in the information stored on the server 22 would be the date the therapy device was used, the duration of the therapy, the heart rate of the patient before, during and after the therapy and the oxygen saturation percentage before, during and after the therapy.

With this stored information, the doctor can retrieve the data and/or a report relating to the data to determine the utilization rate of the therapy, with regard to the length of the therapy as well as the frequency of the therapy, and the effectiveness of the therapy. The doctor can utilize that information to make a determination of whether to continue the therapy or to change the frequency or utilization of the therapy. When the doctor is consulting with the patient about the effectiveness of the therapy, the doctor will at least know that the patient is using the therapy and how often the therapy is being used. Utilization frequency alone is an important factor derived from the data stored on the server 22 as the doctor has no other means by which such information can be obtained.

Furthermore, if the server 22 receives a heart rate or oxygen saturation percentage parameter that is indicative of a possible problem with the patient, the server 22 can communicate with the doctor and possibly with the visiting nurse organization to provide an alert that a possible emergency situation exists. The doctor and/or the visiting nurse organization can then make contact with the patient to confirm if the therapy is being conducted properly, or to confirm that a problem exists for which additional and/or immediate help is needed. Also, if the therapy is not being utilized within predetermined frequency or duration parameters, a communication to the doctor and/or the visiting nurse organization can provide an alert that the therapy is not being properly conducted, whereupon a subsequent contact with the patient can reinforce the need to use the therapy properly and according to the prescription for the therapy.

Figure 3:
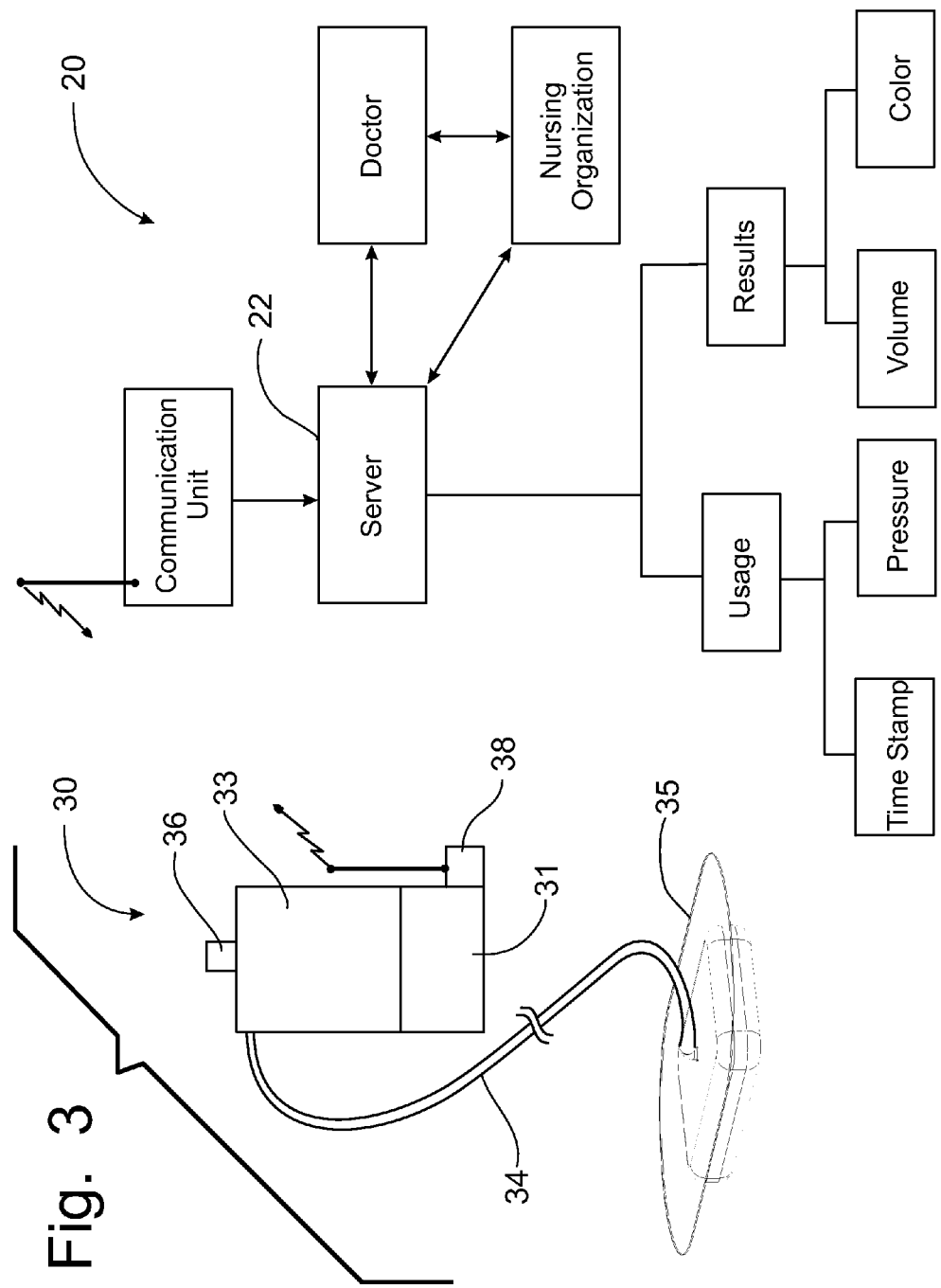
FIG. 3 is a schematic perspective view of a contoured negative pressure bandage for toes as depicted in FIG. 1.

Other therapies can be monitored in a similar manner. One such example is shown in FIG. 3, which is an in-home therapy consisting of a negative pressure bandage apparatus 30 that utilizes a pump 31 to draw a negative pressure on a bandage 35 placed on an open wound of the patient and sealed against the skin around the wound. The negative pressure draws the exudates from the wound into the bandage, or into a storage container 33 mounted on the pump 31, which are typically carried on the person of the patient remotely from the negative pressure bandage 35. Tubing 34 interconnecting the bandage 35 and the storage container 33 conveys the exudates into the storage container 33. A sensor or sensors 36 associated with the storage container 33 can sense a quality of the exudates, for example the color of the exudates, as well as a volume of the exudates collected within the storage container 33.

The communication unit 38 associated with the negative pressure bandage apparatus 30 communicates with the monitoring system 20 to transfer on a periodic basis data related to the operation and effectiveness of the therapy apparatus 30. In the way of example, the information received and stored in the server 22 could provide a time stamp for the particular data being transmitted which would include the sensed quality of the exudates and the volume of the exudates collected. The differential in volume over a measured period of time provides an ongoing collection rate of the exudates from the wound. If the collection rate is above a predetermined parameter a problem with the wound can be identified. Similarly, if the color of the exudates is red, as opposed to a non-red color, the exudates being collected is likely blood, giving an indication that the wound is bleeding more than expected. A collection rate that is too low can indicate that the negative pressure bandage apparatus is not working properly.

Another parameter that can be transmitted to the monitoring system 20 is the pressure gradient being applied by the pump 31. If the pressure gradient is lower than necessary to make the negative pressure bandage 35 operable, there could be a problem with the seal of the band age 35 against the patient's skin around the wound, or an indication that the pump is not working properly. In either case, a visit from the visiting nurse organization is likely called for to determine the problem.

A report or a review of the raw data by the doctor and/or the nurse can provide significant insight as to the proper operation of the therapy 30. If the wound is healing properly, the volume of exudates collected in the storage container 33 would be expected to decrease over time. Such parameters can also be set within the server 22 to provide appropriate indicators to the health care providers. Also, negative pressure bandage apparatus 30 can be used to detect a problem with the wound. If a sudden and dramatic increase in the volume of the exudates collected is detected, a significant problem could be the cause, which can be obviated by an alert issued to the doctor and/or the visiting nurse organization by the server 22.

Many other in-home therapies can be appropriately monitored in a similar manner. Even the dispensing of medication from an appropriately designed medication dispenser having a communication unit (not shown) that would provide a signal to the monitoring system 20 that the medications have been dispensed at the appropriate time. Obviously, the monitoring system will not be able to ascertain that the patient has actually taken the prescribed medication, but the doctor and/or nurse will have feedback from the monitoring system 20 as to the dispensing of the medication. Other possible in-home therapy that could benefit from an application of the monitoring system could be an application of intravenous drugs which could be monitored with an apparatus that identifies the timing of the IV therapy and the volume of the drug administered through the IV set-up.

Figure 4:
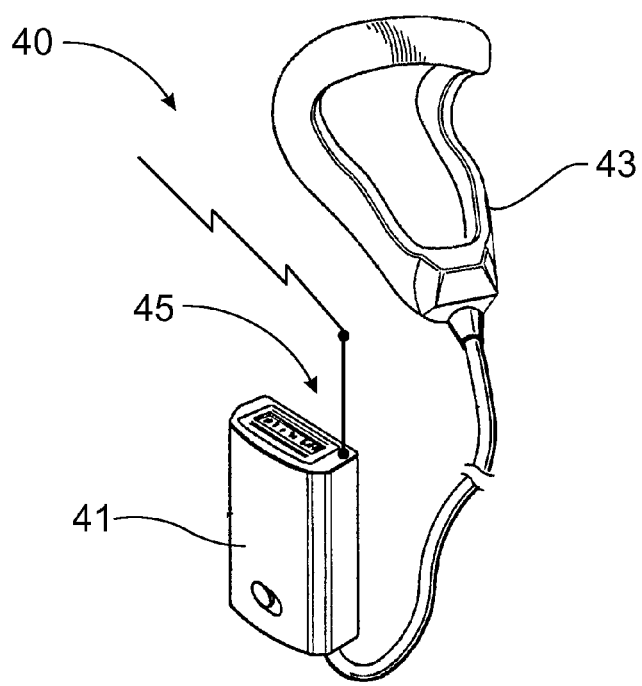
FIG. 4 is a schematic representation of a cervical electromagnetic bone growth stimulation apparatus incorporating the principles of the instant invention.
Figure 5:
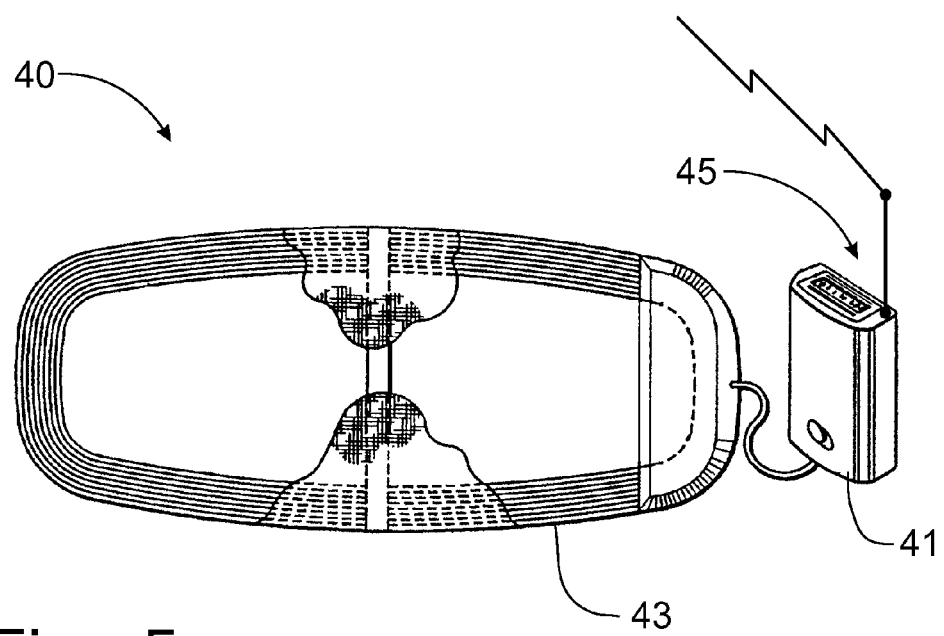
FIG. 5 is a schematic representation of a non-cervical electromagnetic bone growth stimulation apparatus.

Bone growth stimulation therapy is typically applied in the home environment. Electromagnetic bone stimulators 40 are used to apply an electromagnetic field to the site for spinal fusion surgery to stimulate bone growth that fuses the vertebrae together. Such devices, as well as electrical stimulation devices, are typically battery powered and have a control module 41 that regulates the on/off function to send electrical current to a transducer 43 for the generation of an electromagnetic field. The control module 41 can determine the duration of operation of the therapy device 40. An application of a communications transmitter 45 to the control module 41, as is schematically represented in FIGS. 4 and 5, would permit the operation of the bone stimulation therapy device 40 to be monitored. Thus, the patient, as well as the medical professional responsible for the care of the patient, can monitor the operation of the therapy device 40 to determine if the device 40 is being used sufficiently often and for adequate durations to provide proper bone growth therapy.

Through a monitoring system 20 communicating to an off-site server 22 that stores the data transmitted to the monitoring system 20, the health care providers will have real data indicative of the utilization of the therapy, as well as the results obtained through the application of the therapy to the patient. With this data, a health care provider can more effectively determine the parameters by which the therapy is to be conducted. For example, in the inflatable garment therapy apparatus 10, the patient's doctor could decide to change the frequency or duration of the application of the therapy, or even change the timing relative to the sensing of the heart beat for the inflation of the inflation cells to provide a more effective operation of the inflatable garment 15.

The invention of this application has been described above both generically and with regard to specific embodiments. Although the invention has been set forth in what is believed to be the preferred embodiments, a wide variety of alternatives known to those of skill in the art can be selected within the generic disclosure.

Having thus described the invention, what is claimed is:

1. A monitoring system for an externally applied medical therapy apparatus being operated by a patient on whom the medical therapy apparatus is operating in a home environment without benefit of a caregiver, said medical therapy apparatus including a pump having operational functions resulting in operational parameters relating to the effective utilization of the operational functions provided by the medical therapy apparatus, comprising:
    a wireless communications transmitter operatively connected to said pump, said communications transmitter being configured to transmit data relating to the operational functions of the medical apparatus to a remote central station located remotely from said home environment for review by a medical professional located remotely from said home environment, said data including the following operational parameters, a time at which the pump is operated, a length of duration the pump is operated, effectiveness of the operation of the pump, and existence of a malfunction of the pump;
    wherein said medical apparatus is an inflatable garment therapy system and said pump includes a controller for applying pressurized air to an inflatable garment worn by the patient, said controller being operably connected to said communications transmitter to transmit to said remote central station the operational parameters of the inflatable garment therapy system including the heart rate of the patient, the length of time the therapy is utilized and the frequency of operation of the therapy;
    wherein said inflatable garment therapy system further includes a pulse oximeter that determines the oxygen level in an appendage of the patient, said communications transmitter providing feedback to said patient as to the oxygen level to give the patient a positive feedback on the utilization of the inflatable garment therapy system.

2. The monitoring system of claim 1 wherein the effective utilization of the operational functions of the medical therapy apparatus is determined by at least one sensor associated with the pump to ascertain any existence of blood from the patient, a volume of exudates collected by the operation of the pump, a quality of said exudates collected by the pump, a level of oxygen detected in the blood of the patient.

3. The monitoring system of claim 2 wherein said medical apparatus is a negative pressure wound therapy system and said pump is configured to apply a negative pressure to a remote bandage applied to the patient to collect said exudates from a wound on said patient, said pump including sensors for determining pressure applied by said pump, for determining volume of flow of said exudates from said wound, and for determining color of said exudates, said sensors being operably connected to said communications transmitter to provide data thereto for transmission to said remote central station.

4. A method of applying medical therapy to a home-based patient in a home environment irrespective of the presence of an on-site caregiver through use of a medical therapy apparatus having a pump including operational functions resulting in operational parameters relating to the effective utilization of the operational functions provided by the medical therapy apparatus, comprising the steps of:
    sensing said operational parameters of said medical therapy apparatus;
    transmitting said operational parameters of said medical apparatus through a wireless communications transmitter from said pump to a remote central station located remotely from said home environment;
    reviewing said operational parameters of said medical therapy apparatus to determine the effectiveness of said medical therapy by a medical professional accessing the operational parameters at said remote central station at a time independent of the operation of the medical therapy apparatus; and
    communicating with said patient ~ after said reviewing step provides a basis for changes in subsequent operations of said medical therapy apparatus;
    wherein said remote central station sends an alert to said medical professional when one of said operational parameters of said medical therapy apparatus falls outside of a predetermined range of values;
    wherein said medical apparatus is an inflatable garment therapy system and said pump includes a controller for applying pressurized air to an inflatable garment worn by said patient, said transmitting step being accomplished by said controller, said sensing step detecting the heart rate of the patient, the length of time said inflatable garment therapy system is operated, and the frequency at which said inflatable garment therapy system is utilized by said patient.

5. The method of claim 4, wherein said communicating step is accomplished by a caregiver visiting said home-based patient.

6. The method of claim 4, wherein said medical apparatus is a negative pressure wound therapy system and said provides a source of negative pressure by a conduit to a remote bandage covering a wound on said patient to collect exudates from said wound, said sensing step detecting the negative pressure applied by said pump, the volume of flow of said exudates collected from said wound, and the color of said exudates.

7. The method of claim 6 wherein said remote central station alerts said medical professional when the detected color of said exudates indicates a presence of blood in said exudates.

8. The method of claim 6 wherein said pump is operatively coupled to a transmitter that communicates said operational parameters to said remote central station, said reviewing step including said medical professional reviewing said operational parameters from said remote central station to ascertain proper utilization of the medical apparatus and effectiveness of the medical therapy.

* * * * *